United States Patent
Liao et al.

(10) Patent No.: US 9,789,109 B2
(45) Date of Patent: Oct. 17, 2017

(54) MODIFIED ALBUMIN MICROBUBBLE AND METHOD OF MAKING THE SAME

(71) Applicant: National Taiwan University of Science and Technology, Taipei (TW)

(72) Inventors: Ai-Ho Liao, Taipei (TW); Chih-Hung Wang, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 0 days.

(21) Appl. No.: 15/093,757

(22) Filed: Apr. 8, 2016

(65) Prior Publication Data
US 2017/0196863 A1 Jul. 13, 2017

(30) Foreign Application Priority Data
Jan. 7, 2016 (TW) .............................. 105100346 A

(51) Int. Cl.
*A61K 9/127* (2006.01)
*A61K 31/506* (2006.01)
*A61K 9/50* (2006.01)
*A61K 9/00* (2006.01)

(52) U.S. Cl.
CPC .......... *A61K 31/506* (2013.01); *A61K 9/0014* (2013.01); *A61K 9/127* (2013.01); *A61K 9/1277* (2013.01); *A61K 9/5052* (2013.01); *A61K 9/5089* (2013.01)

(58) Field of Classification Search
CPC ................................. A61K 9/127; A61K 9/277
See application file for complete search history.

(56) References Cited

U.S. PATENT DOCUMENTS

| | | | |
|---|---|---|---|
| 4,957,656 A * | 9/1990 | Cerny | A61K 49/223 424/9.52 |
| 5,656,264 A | 8/1997 | Hanada et al. | |
| 8,586,005 B2 | 11/2013 | Walovitch et al. | |
| 2002/0102217 A1 | 8/2002 | Klaveness et al. | |
| 2005/0031544 A1 | 2/2005 | Njemanze | |
| 2008/0045865 A1 | 2/2008 | Kislev | |

(Continued)

FOREIGN PATENT DOCUMENTS

| | | |
|---|---|---|
| CN | 101219224 A | 7/2008 |
| JP | 5801355 B2 | 10/2015 |
| TW | 201332588 A | 8/2013 |

(Continued)

OTHER PUBLICATIONS

Liao et al, "Effectiveness of a Layer-By-Layer Microbubbles-Based Delivery System for Applying Minoxidil to Enhance Hair Growth", Theranostics 6 (6), 817-827, Apr. 11, 2016.*

(Continued)

*Primary Examiner* — Carlos Azpuru
(74) *Attorney, Agent, or Firm* — CKC & Partners Co., Ltd.

(57) ABSTRACT

A modified microbubble is provided. The modified microbubble includes an albumin microbubble and a plurality of chitosan oligosaccharide lactates. The albumin microbubble includes an albumin shell and a gas core inside the albumin shell. The plurality of chitosan oligosaccharide lactates is connected to an outer surface of the albumin shell.

5 Claims, 7 Drawing Sheets

(56) References Cited

U.S. PATENT DOCUMENTS

2013/0041311 A1     2/2013   Kohane et al.
2015/0056273 A1     2/2015   Liao et al.

FOREIGN PATENT DOCUMENTS

TW     201429492 A     8/2014
TW     201500056 A     1/2015
TW     201531308 A     8/2015

OTHER PUBLICATIONS

Messenger AG et al., "Minoxidil: mechanisms of action on hair growth.", British Association of Dermatologists, British Journal of Dermatology, 150, 186-194, 2004.

Friedman ES et al., "Allergic contact dermatitis to topical minoxidil solution: etiology and treatment.", J Am Acad Dermatol 46(2):309-12, Feb. 2002.

Park D, Yoon J, Park J, Jung B, Park H, Seo J, "Transdermal drug delivery aided by an ultrasound contrast agent: an in vitro experimental study.", The Open Biomedical Engineering Journal, 2010, 4, 56-62.

* cited by examiner

US 9,789,109 B2

MODIFIED ALBUMIN MICROBUBBLE AND METHOD OF MAKING THE SAME

RELATED APPLICATIONS

This application claims priority to Taiwan Application Serial Number 105100346, filed Jan. 7, 2016, which is herein incorporated by reference.

BACKGROUND

Field of Disclosure

The present disclosure relates to a modified microbubble.

Description of Related Art

Hair loss disorders generally affect men and women of all ages, and the impact increases with age. Among disorders, androgenetic alopecia (AGA) is the most common form of hair loss, which arises from hair follicles genetically susceptible to androgens. In the susceptible hair follicles, dihydrotestosterone (DHT) binds to the androgen receptor, and the hormone-receptor complex then activates specific genes, which transforms large, terminal follicles to small, miniaturized follicles.

To treat hair loss disorders, Minoxidil (Mx, with the product name of Rogaine®) is the only medication approved by the U.S. Food and Drug Administration (FDA) that can be applied to both men and women so as to reduce hair loss and promote hair growth. However, constant use of Minoxidil is required to work over the long term. Moreover, some patients present with complaints of pruritus and inflammation of the scalp, and the major factor lies in the solvent, propylene glycol, instead of Minoxidil. Though many other solvent candidates are considered, such as butylene glycol, polysorbate, or glycerol, there is no guarantee that these organic solvents do not cause side effects.

On account of this, there is a need for a new prescription of Minoxidil that enables the slowly release of Minoxidil in the target area and the transdermal delivery of Minoxidil to the follicles, shortening the course of hair growth. Meanwhile, the new prescription does not adopt organic solvents to reduce the immunogenicity and inflammations.

SUMMARY

The present disclosure provides a modified microbubble. The modified microbubble includes an albumin microbubble and a plurality of chitosan oligosaccharide lactates. The albumin microbubble includes an albumin shell and a gas core inside the albumin shell. The plurality of chitosan oligosaccharide lactates is connected to an outer surface of the albumin shell.

According to an embodiment of the present disclosure, the modified microbubble further includes a drug connected to the chitosan oligosaccharide lactate to form a drug-carrying modified microbubble.

According to an embodiment of the present disclosure, the drug has a negative charge.

According to an embodiment of the present disclosure, the drug is Minoxidil. The present disclosure provides a modified microbubble, which can be connected to drugs like Minoxidil, and releases drug through ultrasound treatment, enabling the transdermal penetration and absorption by target tissues of drugs to shorten the course of treatments.

According to an embodiment of the present disclosure, the modified microbubble has a diameter of 4,000 nm to 4,400 nm.

The present disclosure also provides a method of making a modified microbubble. The method includes providing an albumin microbubble and connecting a plurality of chitosan oligosaccharide lactates to the albumin microbubble in an environment with a temperature of 0-10° C. to form the modified microbubble.

According to an embodiment of the present disclosure, connecting the plurality of chitosan oligosaccharide lactates to the albumin microbubble in the environment with the temperature of 0-10° C. includes adding a first solution containing the plurality of chitosan oligosaccharide lactates to the albumin microbubble, and the plurality of chitosan oligosaccharide lactates has a concentration of 1-5 mg/ml in the first solution.

According to an embodiment of the present disclosure, the method further includes connecting Minoxidil to the modified microbubble in an environment with a temperature of 0-10° C. to form a drug-carrying modified microbubble.

According to an embodiment of the present disclosure, connecting the Minoxidil to the modified microbubble in the environment with the temperature of 0-10° C. comprises adding a second solution containing Minoxidil to the modified microbubble to form a third solution containing the drug-carrying modified microbubble, and the Minoxidil has a concentration of 1-5 mg/ml in the second solution, and a volume ratio of the first solution to the second solution is 1:1 to 3:1, and the Minoxidil of the drug-carrying modified microbubble has a concentration of 0.1-0.5 mg/ml in the third solution.

According to an embodiment of the present disclosure, the method further includes adjusting a pH of the third solution to 4-6.

BRIEF DESCRIPTION OF THE DRAWINGS

The present disclosure can be more fully understood by reading the following detailed description of the embodiment, with reference made to the accompanying drawings as follows.

DETAILED DESCRIPTION

To comprehensively illustrate the content of the present disclosure in details, references will now be made to embodiments of the present disclosure, examples of which are illustrated in the accompanying drawings. These are, of course, merely examples and are not intended to be limiting. The examples or embodiments can be combined or substituted under preferable circumstances, and one example or embodiment can be affiliated to other examples or embodiments without further illustration or explanation. In the following descriptions, many specific details are elaborated for readers to fully comprehend the following embodiments. Nonetheless, the present invention can also be realized under the conditions without the specific details. In addition, the singular forms "a," "an" and "the" include plural referents unless the context clearly dictates otherwise.

The present disclosure provides a modified microbubble, which can be connected to drugs such as Minoxidil, and act as an ultrasound contrast agent, slowly releasing Minoxidil through ultrasound sonication. This enables the constant release of Minoxidil by ultrasound sonication once it reaches target tissues, and enables the transdermal delivery of Minoxidil to follicles, achieving the effect of shortening hair growth treatments and reducing immunogenicity and inflammations.

Figure 1:
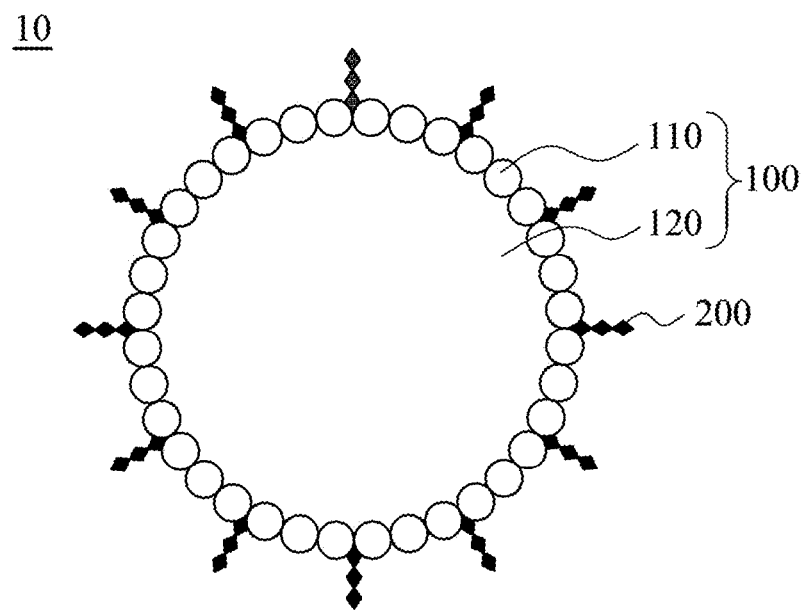
FIG. 1 illustrates a cross-sectional view of a modified microbubble in accordance with some embodiments of the present disclosure.

Referring to FIG. 1, it illustrates a cross-sectional view of a modified microbubble in accordance with some embodiments of the present disclosure. As shown by FIG. 1, the modified microbubble 10 includes an albumin microbubble (MB) 100 and a plurality of chitosan oligosaccharide lactates (COLs) 200. The albumin microbubble 100 includes an albumin shell 110 and a gas core 120 inside the albumin shell 110. In some embodiments, the plurality of chitosan oligosaccharide lactates (COLs) 200 is connected to an outer surface of the albumin shell 110. In some embodiments, the gas core 120 includes a barely soluble gas, such as perfluoropropane ($C_3F_3$) or sulfur hexafluoride ($SF_6$).

Since the albumin carries negative charges, the zeta potential of the albumin shell 110 is below zero, and can thus attract molecules with positive charges. Chitosan oligosaccharide lactates (COLs) 200 contains many amino groups ($-NH_2$), which adhere to protons to form $-NH_3^+$ groups in acidic solutions, making the COL 200 positively charged. Accordingly, the negatively charged albumin shell 110 can be connected to the COL 200 through the electrical attraction, facilitating the COL 200 to be distributed across the outer surface of the albumin shell 110, forming the modified microbubble (COL-MB) 10, which is modified by COL 200.

Figure 2:
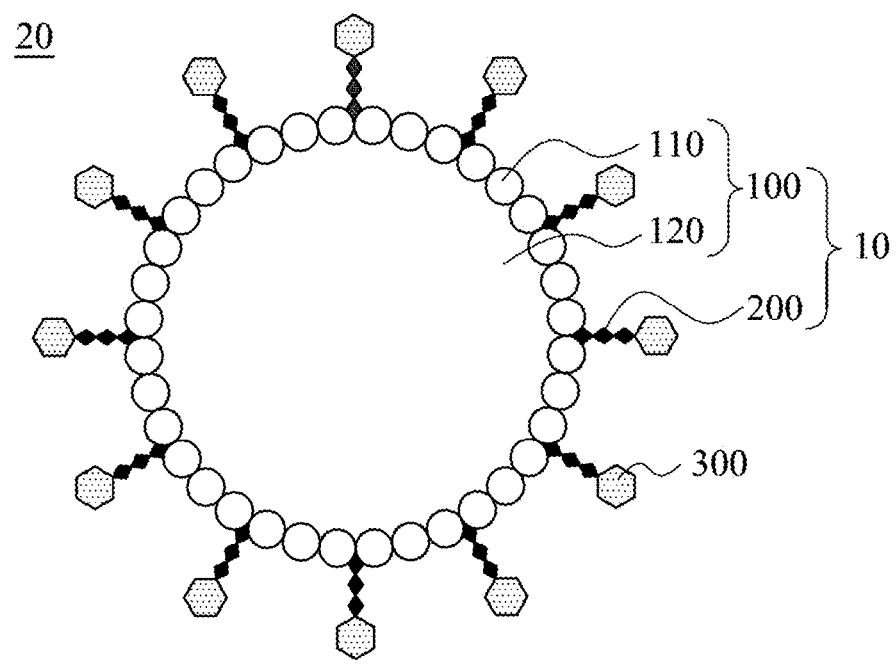
FIG. 2 illustrates a cross-sectional view of a drug-carrying modified microbubble in accordance with some embodiments of the present disclosure.

Referring next to FIG. 2, it illustrates a cross-sectional view of a drug-carrying modified microbubble in accordance with some embodiments of the present disclosure. In some embodiments, the positively charged COL 200 can be further connected to a drug 300 with negative charges. In some embodiments, Minoxidil (Mx) contains a negatively charged oxygen atom, and is thus inclined to be attracted by the $-NH_3^+$ groups of the COL 200 and attached to the COL 200. Thus, as shown in FIG. 2, COLs 200 on the COL-MB 10 can be further connected to the drug 300 (such as Mx), forming the drug-carrying modified microbubble (Mx-COL-MB) 20. It is noted that since both the MB 100 and the Mx 300 carry negatively charges, MB 100 cannot be directly attached to Mx 300, but rather connects to Mx 300 via the COL 200 with positive charges, which makes the drug-carrying modified microbubble (Mx-COL-MB) 20 tend to be electrically neutral.

Compared to conventional, injectable drug-carrying microbubbles where drug encapsulation is required to prevent drug decomposition after entry into the blood, the drug-carrying modified microbubble (Mx-COL-MB) 20 of the present disclosure is externally applied, and thus the drug 300 does not need to be encapsulated, but just need to be attached to the outer surface of the modified microbubble 10. Upon contact with the skin and the ultrasound stimulation, the drug 300 can be released for transdermal penetration.

Figure 3:
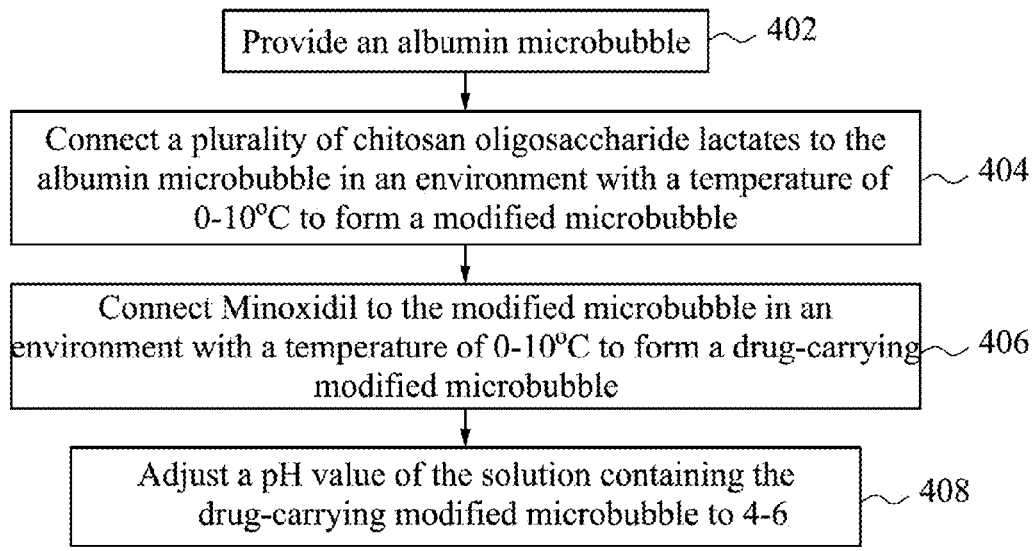
FIG. 3 illustrates a flow chart of making a drug-carrying modified microbubble in accordance with some embodiments of the present disclosure.

Referring to FIG. 3, it illustrates a flow chart of making a drug-carrying modified microbubble in accordance with some embodiments of the present disclosure. In step 402, the method of making the modified microbubble 10 includes providing the albumin microbubble (MB) 100. In various embodiments, 10-30% sterile human serum albumin (HSA) solution is diluted to 1-5% (w/v) HSA stock solution by phosphate-buffered saline (PBS). Then, the $C_3F_8$ or $SF_6$ gas flows into 5-20 mL HSA stock solution and undergo a 1-5 min, 100-300 W ultrasound sonication by a ultrasound sonicator, facilitating the albumin to form shells and encompass the $C_3F_8$ or $SF_6$ gas to form the albumin microbubble (MB) 100. After forming the MB 100, centrifugations are performed to remove the solution and albumins that do not form shells.

Subsequently, in step 404, a plurality of chitosan oligosaccharide lactates (COLs) 200 is connected to the MB 100 in an environment with a temperature of 0-10° C. to form the modified microbubble (COL-MB) 10. In some embodiments, the COL 200 is dissolved in a first solution, and has a concentration of 1-5 mg/ml in the first solution. The first solution can be saline or PBS. In some embodiments, step 404 means adding 1-5 ml of the first solution containing 1-5 mg/ml COL (with the molecular weight of 4,000-6,000) to the MB 100. Then, several times of centrifugations and washing are performed to wipe out the free COL 200, leaving the solution with only COL-MB 10.

Next, in step 406, Minoxidil (Mx) 300 is connected to the modified microbubble 10 in an environment with a temperature of 0-10° C. to form a drug-carrying modified microbubble (Mx-COL-MB) 20. In some embodiments, step 406 includes adding a second solution to the modified microbubble 10, to form a third solution. Mx 300 is dissolved in the second solution, and has a concentration of 1-5 mg/ml in the second solution. The second solution can be saline or PBS. In some embodiments, step 406 includes adding the second solution containing 1-5 mg/ml Mx (with the molecular weight of 209.25) in different volume ratios relative to the first solution, such as 1:1, 1:2, or 1:3, to the solution containing COL-MB 10, and stirring the blended solution at the rate of 10-200 rpm at 0-10° C. for 20-30 hours to form a third solution containing the drug-carrying modified microbubble (Mx-COL-MB) 20. Then, several times of centrifugations and washing are performed to wipe out the free Mx 300. In some embodiments, the Minoxidil 300 attached to the drug-carrying modified microbubble 20 has a concentration of 0.1-0.5 mg/ml in the third solution.

In step 408, a pH of the third solution containing the Mx-COL-MB 20 is adjusted to 4-6. In various embodiments, the pH adjustment is achieved by titration of acids such as the hydrochloric acid or bases such as sodium hydroxide into the third solution to respectively elevate or lower the pH. In some embodiments, the pH of the third solution is adjusted to pH 4.5-5.5, similar to the pH of the human scalp.

Examples

The following examples are meant to elaborate the specific embodiments of the present disclosure in details, and to facilitate those skilled in the art to implement the present disclosure. The following examples are not meant to limit the present disclosure.

Experimental Examples 1-6 and Comparative Examples 1-2

Figure 4A:
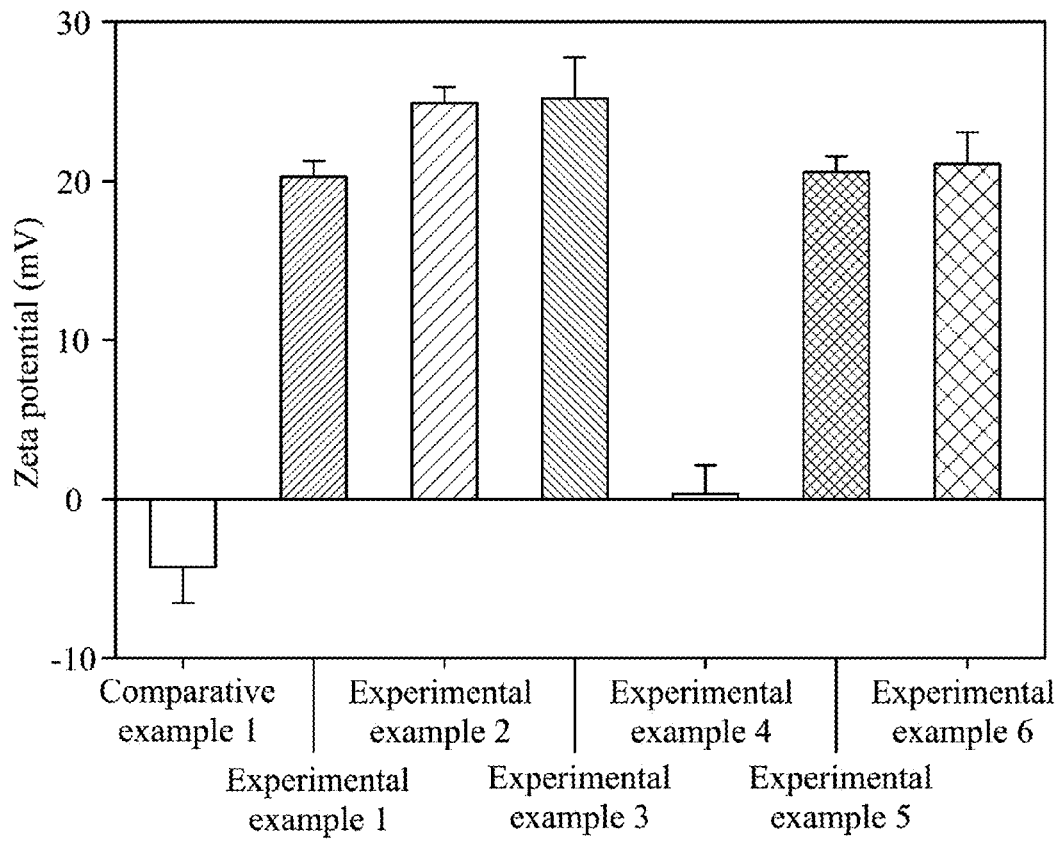
FIG. 4A illustrates a diagram of zeta potentials in accordance with Experimental examples 1-6 and Comparative example 1 of the present disclosure.

Alterations in Zeta Potentials and Particle Diameters Before and after the Modification and Drug Carriage of Microbubbles Referring to FIG. 4A, it illustrates a diagram of zeta potentials in accordance with Experimental examples 1-6 and Comparative example 1 of the present disclosure.

Subsequently, the second solution containing Mx was added to the solutions with COL-MBs (i.e. Experimental examples 1, 2, and 3) to form the third solution containing Mx-COL-MBs (i.e. Experimental examples 4, 5, and 6). In detail, the method of making Experimental examples 4-6 included adding different volumes of the second solution containing 2 mg/ml Mx to Experimental examples 1-3 respectively, and performing blending at 4° C. for 24 hours. The volume ratios of the second solution to the first solution in Experimental example 4-6 were 1:1, 1:2, and 1:3 respectively. As shown in FIG. 4A and the above Table 1, the zeta potential of Experimental example 4 was greatly reduced to 0.41±1.73 mV, while the zeta potentials of Experimental examples 5 and 6 only slightly decreased to 20.54±1.02 mV and 21.10±1.97 mV respectively. This indicates that when the solution volume ratio of Mx:COL is 1:1 (i.e. Experimental example 4), the COL can be attached to maximal amount of the Mx, with the Mx attaching efficiency reaching 14.87±0.03%, causing the concentration of attached Mx in the third solution to reach about 0.3 mg/ml, and the zeta potential to have the maximal slump to reduce to near zero and electrically neutral to be easily dissolve in the saline (such as PBS).

Figure 4B:
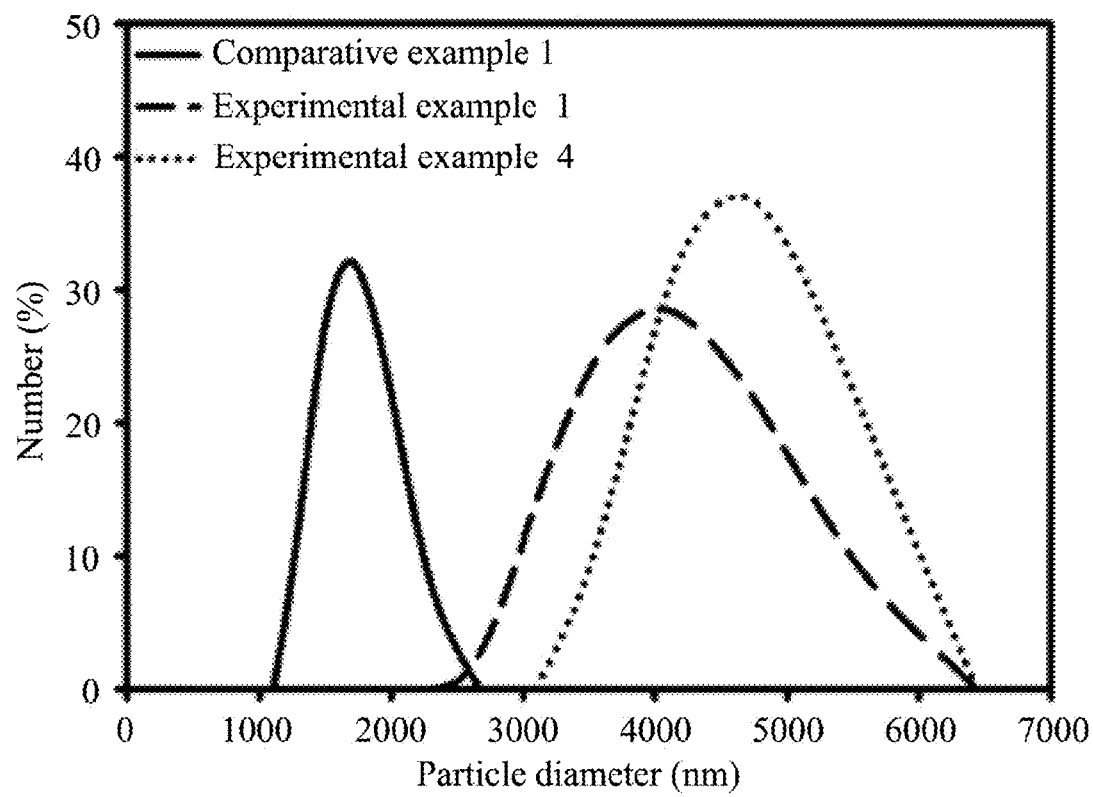
FIG. 4B illustrates a diagram of particle diameters against quantity in accordance with Experimental examples 1 and 4 and Comparative example 1 of the present disclosure.

Referring to FIG. 4B, it illustrates a diagram of particle diameters against quantity in accordance with Experimental examples 1 and 4, and Comparative example 1 of the present disclosure. As shown in FIG. 4B and the above Table 1, the particle diameter of Comparative example 1 was about 1550±270 nm, the particle diameter of Experimental example 1 was in the range between 4,000 nm to 4,400 nm,

TABLE 1

|  |  | Zeta potential (mV) | Particle diameter (μm) | Mx attaching efficiency (%) |
| --- | --- | --- | --- | --- |
| Comparative example 1 | MBs | −3.87 ± 2.78 | 1.55 ± 0.27 | — |
| Comparative example 2 | MBs + Mx | −0.43 ± 1.01 | 1.46 ± 0.30 | 2.55 ± 0.15 |
| Experimental example 1 | COL-MBs (1:1) | 20.23 ± 1.20 | 4.15 ± 0.17 | — |
| Experimental example 2 | COL-MBs (2:1) | 24.98 ± 1.10 | 4.36 ± 0.05 | — |
| Experimental example 3 | COL-MBs (3:1) | 25.23 ± 2.60 | 4.25 ± 0.82 | — |
| Experimental example 4 | Mx-COL-MBs (1:1) | 0.41 ± 1.73 | 4.50 ± 0.10 | 14.87 ± 0.03 |
| Experimental example 5 | Mx-COL-MBs (2:1) | 20.54 ± 1.02 | 4.69 ± 0.27 | 11.68 ± 0.01 |
| Experimental example 6 | Mx-COL-MBs (3:1) | 21.10 ± 1.97 | 4.30 ± 0.12 | 10.90 ± 0.01 |

As shown in FIG. 4A and the above Table 1, Comparative example 1 represented unmodified microbubbles (MBs) with the zeta potential of −3.87±2.78 mV. Comparative example 2 (not shown in FIG. 4A) represented unmodified microbubbles and unattached Minoxidil (MBs+Mx) with the zeta potential slightly raised to −0.43±1.01 mV, while the Mx attaching efficiency was only 2.55±0.15%.

By blending a fixed amount of MBs with COL in different volume ratios, COL-MBs with different contents of COL were formed. In detail, the method of making Experimental examples 1-3 included adding different volumes of the first solution containing 2 mg/ml COL to the fixed amount of MBs (with the volume ratio of COL:MB to be 1:1, 2:1, and 3:1), and performing blending at 4° C. for 24 hours to form the COL-MBs (1:1) (Experimental example 1), the COL-MBs (2:1) (Experimental example 2), and the COL-MBs (3:1) (Experimental example 3). The zeta potentials of Experimental examples 1-3 were 20.23±1.20 mV, 24.98±1.10 mV, and 25.23±2.60 mV respectively, which exhibited that the negatively charged MB could be attached to a great amount of positively charged COLs, resulting in a great increase in the zeta potentials of COL-MBs.

or about 4150±170 nm, indicating great increase in particle diameter after the connection of the MB to the COL. The particle diameter of Experimental example 4 is about 4500±100 nm, indicating no great increase in particle diameter after the connection of the Mx to the COL.

Figure 4C:
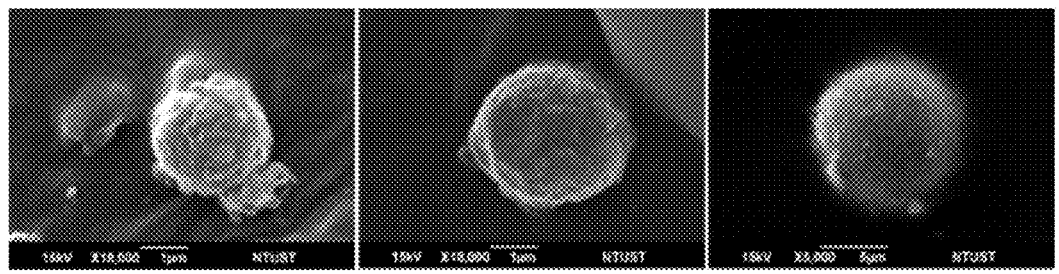
FIG. 4C illustrates scanning electron microscopy images in accordance with Experimental examples 1 and 4 and Comparative example 1 of the present disclosure.

Referring to FIG. 4C, it illustrates scanning electron microscopy images in accordance with Experimental examples 1 and 4 and Comparative example 1 of the present disclosure. As shown in FIG. 4C, Comparative example 1 manifested a rough surface due to irregular albumin particles, Experimental example 1 exhibited smoother surface due to connection to the COL, while Experimental example 4 was comparably the most smoothest due to connection to the Mx.

Experimental Examples 1' and 4' and Comparative Example 1', 3, 4 and 5

Alterations in Post-Destruction Absorbance Spectra Before and after the Modification and Drug Carriage of Microbubbles Microbubbles were ultrasound contrast agents, which could give rise to the effect of inertial cavitation and be destroyed under ultrasound (US) sonication of certain intensity and period of time. This study compared 3 kinds of destroyed microbubbles, namely the destroyed MB (Comparative example 1'), destroyed COL-MB (Experimental example 1'), and destroyed Mx-COL-MB (Experimental example 4'), to non-microbubble comparative examples, namely the albumin (Comparative example 3), the Mx (Comparative example 4), and the saline (Comparative example 5), to look into the alterations in post-destruction absorbance spectra before and after the modification and drug carriage of microbubbles.

Figure 5:
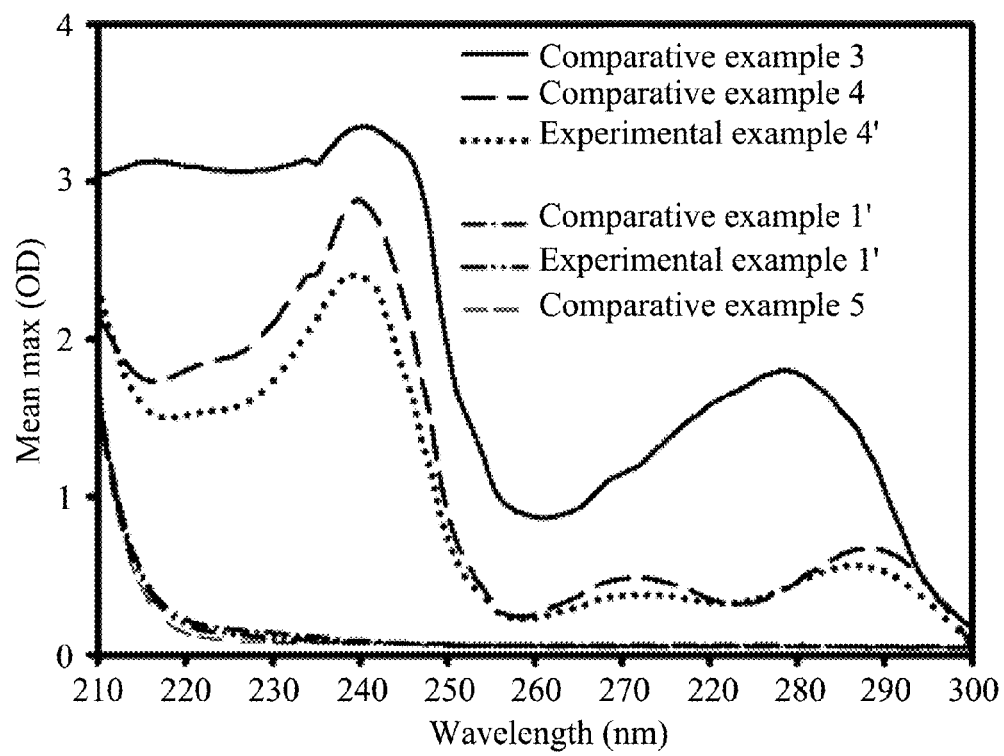
FIG. 5 illustrates a diagram of absorbance spectra in accordance with Experimental examples 1' and 4' and Comparative examples 1', 3, 4 and 5 of the present disclosure.

Referring to FIG. 5, it illustrates a diagram of absorbance spectra in accordance with Experimental examples 1' and 4' and Comparative examples 1', 3, 4 and 5 of the present disclosure. As shown in FIG. 5, compared to Comparative examples 3 and 4 which had the specific absorption peaks, neither Comparative example 1' nor Experimental example 1' absorbed lights of specific wavelengths, which was the same as Comparative example 5. However, Experimental example 4' absorbed lights at the wavelength of 230 nm, 261 nm, and 285 nm, which was the same as the absorption spectrum of Comparative example 4, indicating that the destroyed Mx-COL-MB released Mx.

Experimental Examples 7-10

In Vitro Drug Release Study of the Mx-COL-MB

The study measured the Mx release pattern of the Mx-COL-MB through dialysis method after ultrasound (US) treatment. The Mx-COL-MBs were divided into 4 kinds of environments, which were the Experimental example 7 at pH 4 with ultrasound treatment, Experimental example 8 at pH 4 without ultrasound treatment, Experimental example 9 at pH 7.4 with ultrasound treatment, and Experimental example 10 at pH 7.4 without ultrasound treatment. The procedures of the study included: loading 3 ml of PBS suspension solution containing any one of the Experimental examples 7-10 into a dialysis bag, and dialyzing the suspension solution against the PBS release medium at the same pH. The dialysis temperature was 37±0.5° C., accompanied with magnetic stirring at 600 rpm. At the $0.5^{th}$ hr, the 1-MHz ultrasound sonicator was positioned 3 mm from the top of the dialysis bag and performed ultrasound sonication at a power density of 3 W/cm² for 1 min. At the time intervals of 0.1, 0.2, 0.3, 0.4, 0.5, 1, 2, 3, 4, 5, and 6 hours, 1 ml of sample was taken out from the release medium to measure the content of Mx dialyzed into the sample, and the same volume of PBS was supplemented into the release medium. The accumulative release percentage of Mx was calculated according to the following equation:

$$R = \frac{c_n v_0 + \sum_{i=0}^{n-1} c_i v_i}{W} \times 100\%$$

where R is the release rate, $c_n$ is the drug concentration in the total release medium at each time interval of sampling, $c_i$ is the drug concentration in the previous release medium sample, $v_0$ is the total volume of the release medium, $v_i$ is the volume of the release medium sample, and W is the total drug content of the release sample.

Figure 6:
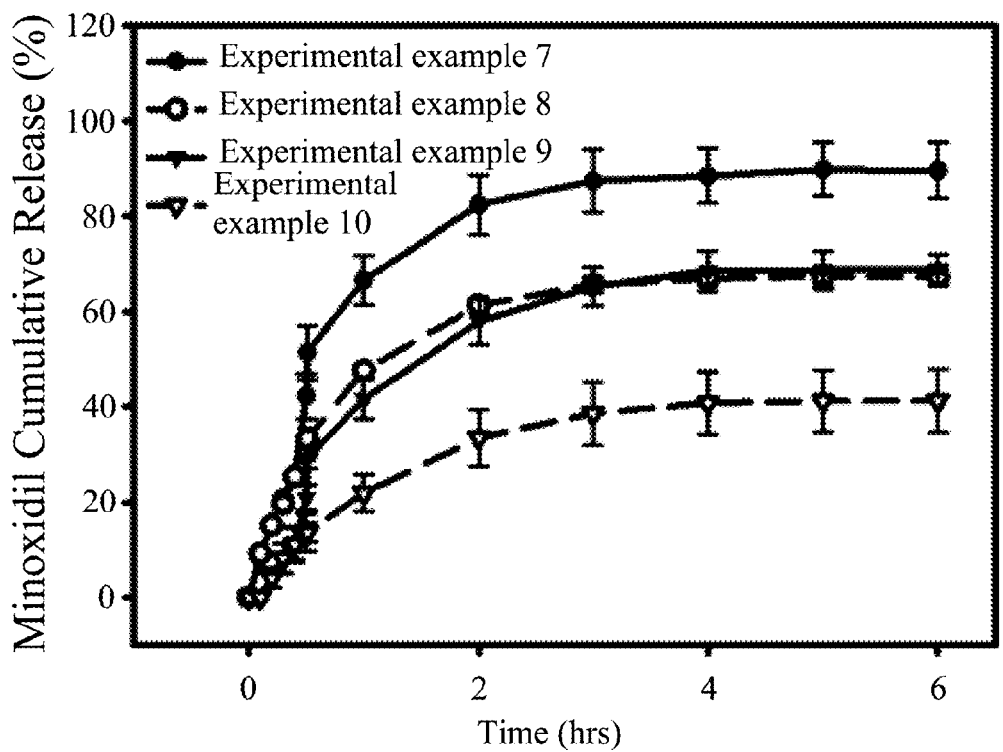
FIG. 6 illustrates a diagram of cumulative release rates of Minoxidil against time in accordance with Experimental examples 7-10 of the present disclosure.

Referring to FIG. 6, it illustrates a diagram of cumulative release rates of Minoxidil against time in accordance with Experimental examples 7-10 of the present disclosure. As shown in FIG. 6, the cumulative Mx release rate of Experimental example 10 at the $0.5^{th}$ hr was only 13.6%, while the cumulative Mx release rate of Experimental example 9 at the same time was 29.2%. The cumulative Mx release rate of Experimental example 8 at the $0.5^{th}$ hr was 30.3%, while the cumulative Mx release rate of Experimental example 7 at the same time was 51.4%. Without US sonication, the Mx release was significantly limited. The cumulative Mx release rate of Experimental example 10 at the $6^{th}$ hr was only 41.2%, while the cumulative Mx release rate of Experimental example 8 at the $6^{th}$ hr was 67.3%. However, after US treatment, the Mx-COL-MB constantly and slowly released the Mx. The cumulative Mx release rate of Experimental example 9 at the $6^{th}$ hr reached 68%, while the cumulative Mx release rate of Experimental example 7 at the $6^{th}$ hr reached 89%. Hence, US treatment elevated the Mx release rate of the Mx-COL-MB by 20-26%, while pH 4 also elevated the Mx release rate. Since the pH of the human scalp is coincidently about pH 4.5-5.5, when Mx-COL-MB contacts the scalp with combined ultrasound sonication at 3 W/cm² for 1 min, Mx can be rapidly released.

Experimental Example 11 and Comparative Examples 6-7

Study of Transdermal Penetration Depth

The study includes 3 groups of solutions: Comparative example 6 without MBs added and without US treatment, the US group without MBs added while with US treatment (Comparative example 7), and the US+MBs group with 500 μl MBs added and US treatment (Experimental example 11). Each group contained 0.1 mg FITC (fluorescein isothiocyanate), and was uniformly loaded onto the porcine ear skin with an area of 4.5 cm² and a thickness of 3 mm, sonicated by the 1-MHz ultrasound sonicator successively at power density of 3 W/cm², with each sonication period of 1 min. After sonication, the FITC (and the MBs) retained on the porcine ear skin for 6 hr, and was then washed away.

Figure 7:
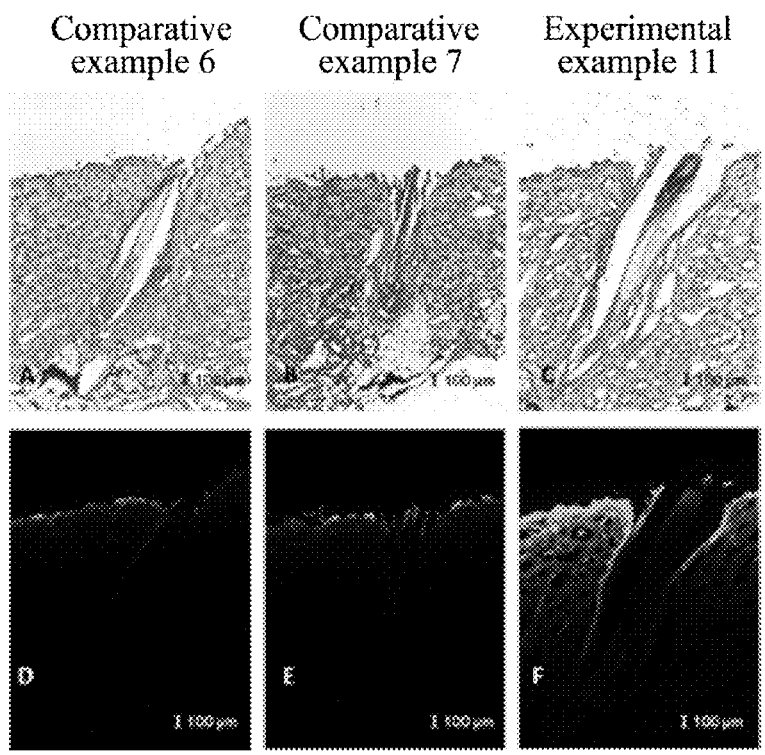
FIG. 7 illustrates scanning electron microscopy images of transdermal delivery of fluorescent agents in accordance with Experimental example 11 and Comparative examples 6 and 7 of the present disclosure.

Referring to FIG. 7, it illustrates scanning electron microscopy images of transdermal delivery of fluorescent agents in accordance with Experimental example 11 and Comparative examples 6 and 7 of the present disclosure. FIG. 7A-7C are bright-field images, and FIG. 7D-7F are dark-field fluorescent images. FIGS. 7A and 7D represent Comparative example 6, whose penetration depth of FITC was 312±19 μm. FIGS. 7B and 7E represent Comparative example 7, whose penetration depth of FITC was 405±23 μm. In contrast, FIGS. 7C and 7F represent Experimental example 11, whose penetration depth of FITC reached 1856±45 μm. This indicates that after US treatment, the skin permeability is increased, and further with the effect of the MB, transdermal penetration of drugs can be effective.

Experimental Examples 4 and 12 and Comparative Examples 1, 4, 8 and 9

Transdermal Penetration Study of Mx Released by Mx-COL-MBs

The study included 6 groups of solutions: groups without ultrasound treatment including the Mx group (Comparative example 4), the MBs groups (Comparative example 1), and the Mx-COL-MBs group (Experimental example 4), and groups with ultrasound treatment including the US+Mx group (Comparative example 8), the US+MBs+Mx groups (Comparative example 9), and the US+Mx-COL-MBs group (Experimental example 12). In Comparative examples 4, 8, and 9, the concentration of Mx was 0.3 mg/ml, while in Experimental examples 4 and 12, the concentration of Mx carried by the Mx-COL-MB was 0.3 mg/ml. The procedures of the study included: interposing a piece of 3 mm-thick porcine ear skin between a donor cell and a receptor cell of the Franz diffusion cell at a temperature of 37±0.5° C. 1 ml of any one of the abovementioned 6 solutions was applied to the donor cell facing the stratum corneum (SC) side, enabling the MB, Mx, or Mx-COL-MB to penetrate the Parafilm on a bottom of the donor cell and reach the skin. Besides, the receptor cell facing the dermis side was filled with 12 ml of PBS at pH 7.4, accompanied with magnetic stirring at the rate of 600 rpm and 0.01% gentamicin to prevent bacterial degradation of the Mx during the penetration process. At the $0.5^{th}$ hr, a 1-MHz ultrasound sonicator was positioned 3 mm from the top of the skin, and the skin was sonicated at a power density of 3 W/cm² for 1 min. At the time intervals of 0.5, 1, 2, 3, 4, 5, 6, 8, 12 and 18 hours, 1 ml of receptor solution sample filtered by 0.2-μm pores was extracted from the receptor cell to measure the Mx content in the receptor solution, with the receptor solution refilled each time with the same volume of PBS. After 18 hours, the porcine skin sample was washed and then homogenized with 1 ml of the receptor solution. The supernatant was centrifuged to acquire further supernatant to measure the absorbed amount of Mx in the porcine ear skin.

Figure 8:
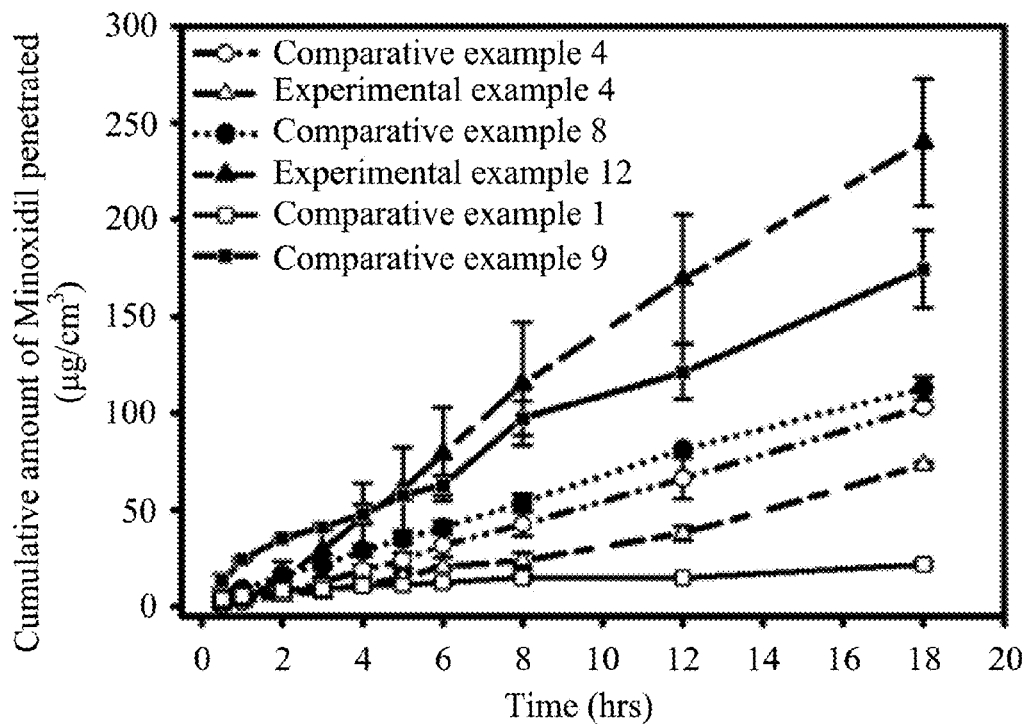
FIG. 8 illustrates a diagram of cumulative penetration amounts of Minoxidil against time in accordance with Experimental examples 4 and 12 and Comparative examples 1, 4, 8 and 9 of the present disclosure.

Referring to FIG. 8, it illustrates a diagram of cumulative penetration amounts of Minoxidil against time in accordance with Experimental examples 4 and 12 and Comparative examples 1, 4, 8 and 9 of the present disclosure. As shown in FIG. 8, although Comparative example 9 induced rapid Mx penetration with the amount of 62.9±5.0 μg/cm³ in the first 6 hours, the penetration amount gradually sloped gently in 8-18 hours. Relatively, the Mx penetration amount of Experimental example 12 reached 240.0±32.8 μg/ml at the $18^{th}$ hour, which was significantly higher than the amount of 174.3±19.8 μg/ml in Comparative example 9, the amount of 113.0±6.0 μg/ml in Comparative example 8, the amount of 103.1±0.5 μg/ml in Comparative example 4, the amount of 73.3±1.4 μg/ml in Experimental example 4, and the amount of 21.7±1.6 μg/ml (the background) in Comparative example 1. This indicated that after ultrasound treatment of the Mx-COL-MBs and MBs+Mx (i.e. Experimental examples 12 and 9), the Mx penetration amount could increase by 2.3 and 1.7 folds compared to the Mx group (Comparative example 4) respectively. Therefore, in Experimental example 12, the US-treated Mx-COL-MB could exhibit the highest amount of Mx penetration in 18 hours.

with US treatments exhibits not only the highest Mx amount of cumulative penetration, but also highest Mx amount of skin penetration, facilitating the amount of transdermally penetrated Mx to be the highest.

Experimental Example 12 and Comparative Examples 4, 8, 9 and 10

Study of Animal Hair Growth

The study utilized 6-week-old C57BL/6 mice weighing 20-25 g, which were shaved at an area of about 10☐cm² in the back at 8 weeks old, when all of the hair follicles were synchronized in the telogen phase. The mice were divided into 5 groups including: the untreated group (Comparative example 10), the Mx group with only Mx provided (Comparative example 4), the US group with Mx and US treatment provided (Comparative example 8), the US+MBs group with Mx, MBs, and US treatment provided (Comparative example 9), the US+Mx-COL-MBs group with Mx-COL-MBs and US treatment provided (Experimental example 12). Among all groups, the US treatment was applied at 3 W/cm² for 1 min, and the concentration of Mx was 0.3 mg/ml (i.e. 0.5 ml/cm²) in all groups. The change in skin luminosity of the shaved area was assessed using the Chroma Meter. The hair growth rate was calculated according to the following equation:

Hair growth rate (%)=$(L_1-L_n)/L_1 \times 100\%$ where $L_1$ is the luminosity index of the shaved area, and $L_n$ is the luminosity index of the area at different time intervals.

Figure 9:
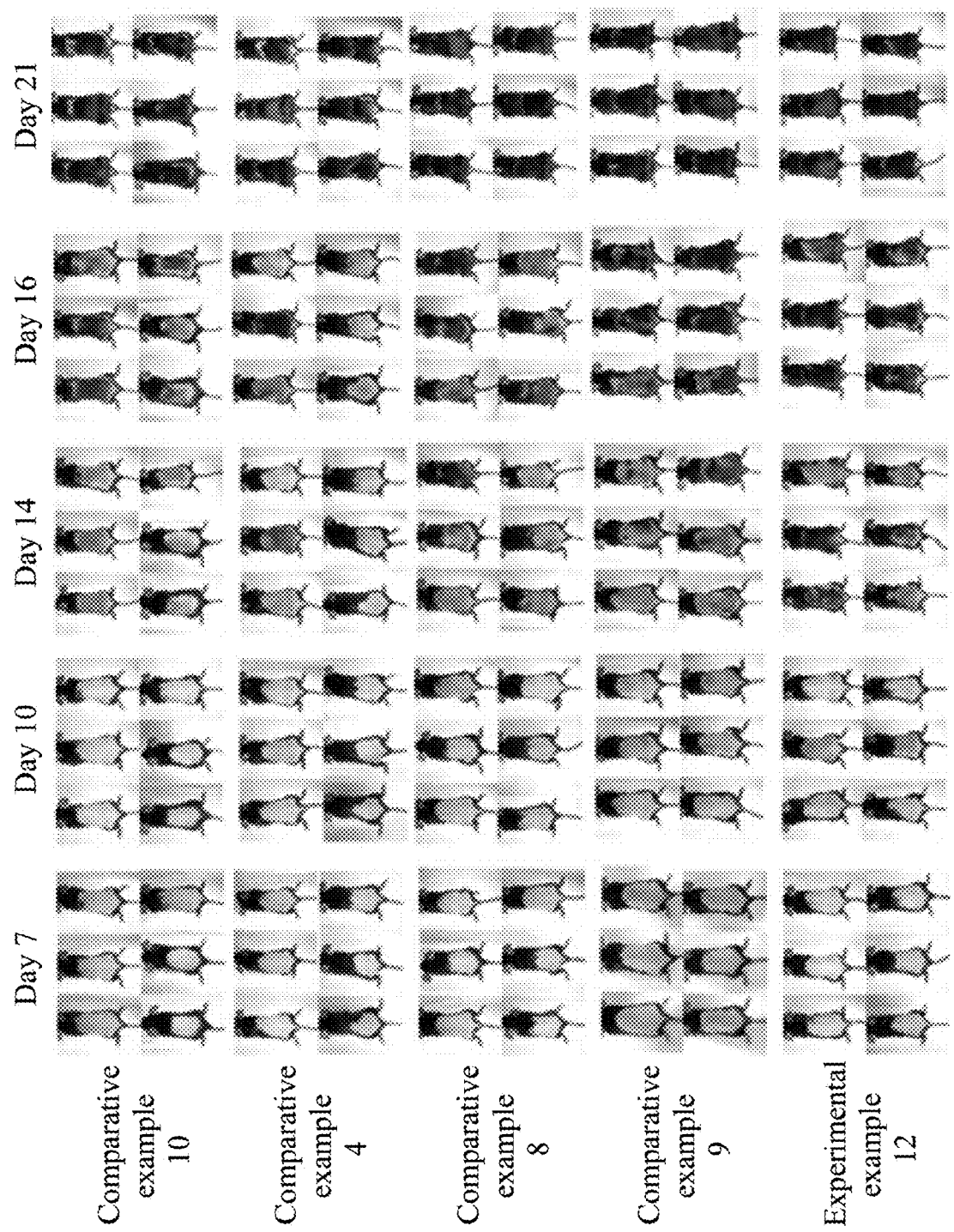
FIG. 9 illustrates top-view observation images of hair growth of mice backs against time in accordance with Experimental example 12 and Comparative examples 4, 8, 9 and 10 of the present disclosure.

Referring to FIG. 9, it illustrates top-view observation images of hair growth of mice backs against time in accordance with Experimental example 12 and Comparative examples 4, 8, 9 and 10 of the present disclosure. As show in FIG. 9, at day 10, the numbers of mice with significantly lower skin luminosity were: 5 in Experimental example 12, 3 in Comparative example 9, 1 in Comparative example 8, 1 in Comparative example 4, and 0 in Comparative example 10, indicating the most rapid hair growth in Experimental example 12. At day 14, hair growth rates of each mouse in Experimental example 12 were more significant than the rates of the rest four groups.

Figure 10:
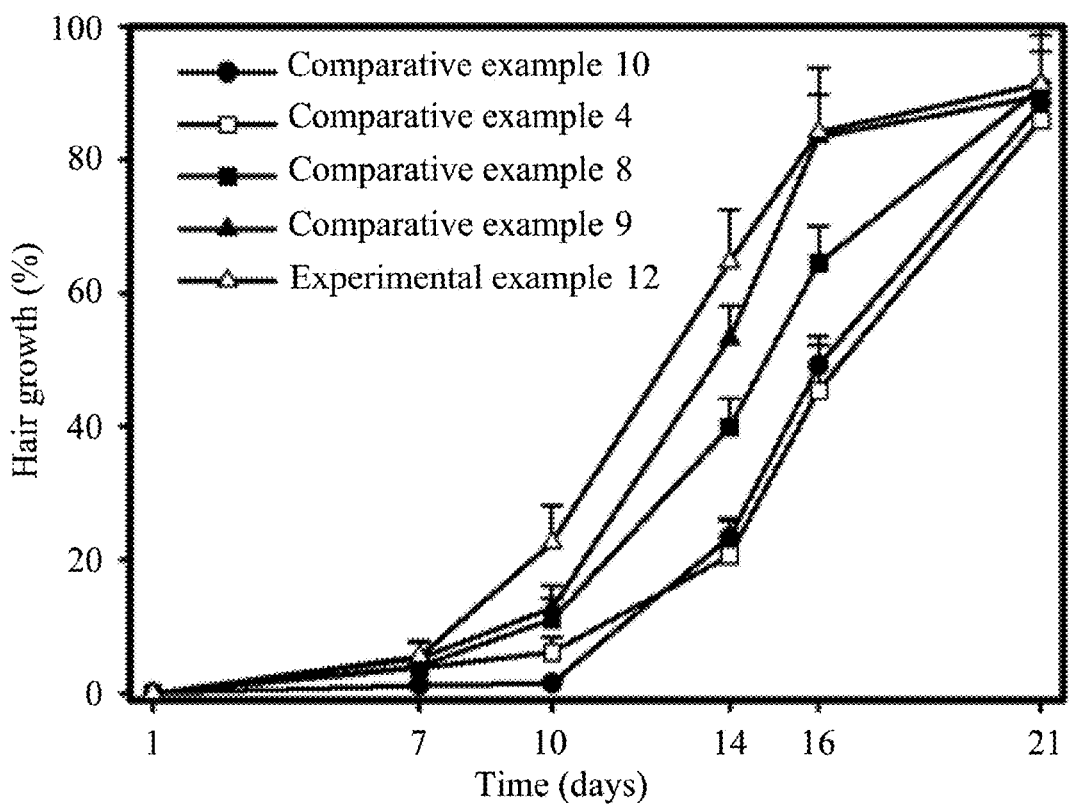
FIG. 10 illustrates a diagram of hair growth rates of mice backs against time in accordance with Experimental example 12 and Comparative examples 4, 8, 9 and 10 of the present disclosure.

Referring to FIG. 10, it illustrates a diagram of hair growth rates of mice backs against time in accordance with Experimental example 12 and Comparative examples 4, 8, 9

TABLE 2

| Group | Skin weight (g) | Amount of skin absorption (μg/ml) | Amount of skin penetration (μg/ml) | Amount of total penetration (μg/ml) |
| --- | --- | --- | --- | --- |
| Comparative example 4 | 0.1659 ± 0.0325 | 52.42 ± 9.55 | 103.1 ± 0.51 | 155.54 ± 10.05 |
| Comparative example 8 | 0.1557 ± 0.0198 | 33.02 ± 1.56 | 113.01 ± 5.95 | 126.04 ± 7.52 |
| Comparative example 9 | 0.1654 ± 0.0214 | 27.33 ± 2.73 | 174.34 ± 14.01 | 201.68 ± 16.74 |
| Experimental example 4 | 0.1845 ± 0.0376 | 26.75 ± 3.98 | 73.26 ± 1.42 | 100.01 ± 5.40 |
| Experimental example 12 | 0.1430 ± 0.0253 | 17.43 ± 1.12 | 240.04 ± 32.82 | 257.48 ± 33.94 |

Referring to the above Table 2, in terms of the amount of skin absorption, the Mx amount of skin absorption reached 52.42±9.55 μg/ml in Comparative example 4, which was significantly higher than Comparative example 8, Comparative example 9, Experimental example 4, and Experimental example 12. Nevertheless, in terms of the amount of skin penetration, the amount of skin penetration in the Experimental example 12 reached 240.04±32.82 μg/ml, significantly higher than the other groups. Thus, Mx-COL-MBs and 10 of the present disclosure. As shown in FIG. 10, at day 10 and 14, the hair growth rate of Experimental example 12 increased by 22.6% and 64.7% respectively compared to day 1, significantly higher than the rates of the rest four groups. At day 16, the hair growth rate of Experimental example 12 reached 84.2%, higher than the 49.2% of Comparative example 10, the 45.5% of Comparative example 4, the 64.5% of Comparative example 8, and the 83.5% of Comparative example 9.

Figure 11:
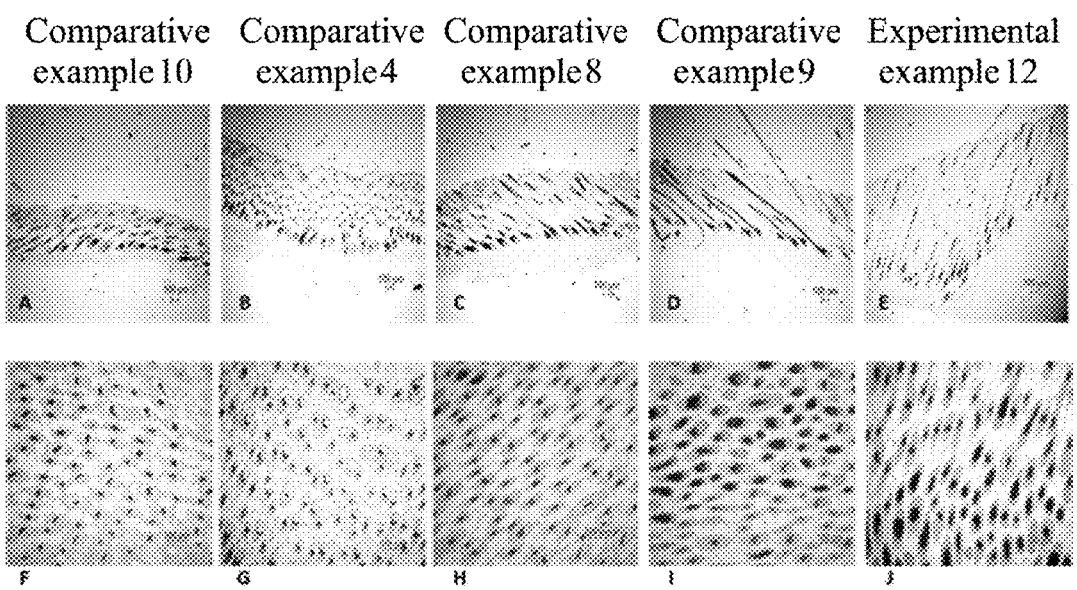
FIG. 11 illustrates scanning electron microscopy histological images of mice backs in accordance with Experimental example 12 and Comparative examples 4, 8, 9 and 10 of the present disclosure.

Referring to FIG. 11, it illustrates scanning electron microscopy histological images of mice backs in accordance with Experimental example 12 and Comparative examples 4, 8, 9 and 10 of the present disclosure. FIG. 11A-11E demonstrate vertical view of hair follicles, and FIG. 11F-11J demonstrate coronal view of hair follicles. FIGS. 11A and 11F illustrate Comparative example 10. FIGS. 11B and 11G illustrate Comparative example 4. FIGS. 11C and 11H illustrate Comparative example 8. FIGS. 11D and 11I illustrate Comparative example 9. FIGS. 11E and 11J illustrate Experimental example 12. As shown in FIG. 11A-11E, at day 21, Comparative example 4 exhibited significantly increased skin thickness, Comparative example 8 exhibited increased hair length, Comparative example 9 exhibited hair growth with even longer hair, while Experimental example 12 exhibited the most significantly increased skin thickness and hair length with promoted elongation of hair follicles from the epidermis down to the subcutis in a vertical section. In FIG. 11F-11J, although the number of hair follicles didn't increase significantly after treatments among all groups, Comparative example 8, Comparative example 9, and Experimental example 12 all exhibited increase in the diameter of the keratinized hair shafts and the size of hair follicles, with Comparative example 9 and Experimental example 12 showing a more significant level of increase, and Experimental example 12 showing the most significant increase in the elongation of the hair follicle section.

In summary, the present disclosure applies the drug-carrying modified microbubble (Mx-COL-MB) dissolved in PBS to skin externally, and performs ultrasound (US) treatment to prompt the Mx-COL-MB to release a great amount of Minodixil (Mx), while the Mx can undergo transdermal penetration to reach the hair follicle to significantly enhance the hair growth rate, which achieves the effects of shortening the course of hair growth treatments and reduction in the sensitive skin reactions.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method of making a modified microbubble, comprising:
   providing an albumin microbubble, comprising:
      supplying gas into an albumin solution; and
      sonicating the albumin solution to form an albumin shell encompassing the gas to form the albumin microbubble; and
   connecting a plurality of chitosan oligosaccharide lactates to the albumin microbubble in an environment with a temperature of 0-10° C. to form the modified microbubble.

2. The method of claim 1, wherein connecting the plurality of chitosan oligosaccharide lactates to the albumin microbubble in the environment with the temperature of 0-10° C. comprises adding a first solution comprising the plurality of chitosan oligosaccharide lactates to the albumin microbubble, and the plurality of chitosan oligosaccharide lactates has a concentration of 1-5 mg/ml in the first solution.

3. The method of claim 2, further comprising:
   connecting Minoxidil to the modified microbubble in an environment with a temperature of 0-10° C. to form a drug-carrying modified microbubble.

4. The method of claim 3, wherein connecting the Minoxidil to the modified microbubble in the environment with the temperature of 0-10° C. comprises adding a second solution comprising the Minoxidil to the modified microbubble to form a third solution comprising the drug-carrying modified microbubble, and the Minoxidil has a concentration of 1-5 mg/ml in the second solution, and a volume ratio of the first solution to the second solution is 1:1 to 3:1, and the Minoxidil of the drug-carrying modified microbubble has a concentration of 0.1-0.5 mg/ml in the third solution.

5. The method of claim 4, further comprising adjusting a pH value of the third solution to 4-6.

* * * * *